US012324824B2

(12) United States Patent
Del Bono et al.

(10) Patent No.: US 12,324,824 B2
(45) Date of Patent: Jun. 10, 2025

(54) FOOD SUPPLEMENT, FOR AS ADJUVANT, FOR PREVENTING VASCULAR DEMENTIA

(71) Applicant: CRISTALFARMA S.R.L., Milano MI (IT)

(72) Inventors: Maria Cristina Del Bono, Milano MI (IT); Francesco Bonomo, Milano MI (IT)

(73) Assignee: CRISTALFARMA S.R.L., Milano MI (IT)

( * ) Notice: Subject to any disclaimer, the term of this patent is extended or adjusted under 35 U.S.C. 154(b) by 673 days.

(21) Appl. No.: 17/630,988

(22) PCT Filed: Jul. 24, 2020

(86) PCT No.: PCT/IB2020/056996
§ 371 (c)(1),
(2) Date: Jan. 28, 2022

(87) PCT Pub. No.: WO2021/019395
PCT Pub. Date: Feb. 4, 2021

(65) Prior Publication Data
US 2022/0265752 A1 Aug. 25, 2022

(30) Foreign Application Priority Data

Aug. 1, 2019 (IT) .................. 102019000013707

(51) Int. Cl.
A61K 36/53 (2006.01)
A61K 9/00 (2006.01)
A61K 9/16 (2006.01)
A61K 31/164 (2006.01)
A61K 31/355 (2006.01)
A61K 36/23 (2006.01)

(52) U.S. Cl.
CPC ............ A61K 36/53 (2013.01); A61K 9/0053 (2013.01); A61K 9/16 (2013.01); A61K 31/164 (2013.01); A61K 31/355 (2013.01); A61K 36/23 (2013.01)

(58) Field of Classification Search
None
See application file for complete search history.

(56) References Cited

U.S. PATENT DOCUMENTS

2003/0157201 A1* 8/2003 Pandita .................. A61K 36/23
514/100

FOREIGN PATENT DOCUMENTS

| CN | 102389437 A | 3/2012 |
|---|---|---|
| CN | 105287985 A | 2/2016 |
| CN | 107789429 A | 3/2018 |
| CN | 109419800 A | 3/2019 |
| JP | 2000229854 A | 8/2000 |
| KR | 20120051458 A | 5/2012 |
| WO | 2003003981 A2 | 1/2003 |
| WO | 2013066151 A1 | 5/2013 |

OTHER PUBLICATIONS

Farooq et al. (2013) Curr. Artheroscler. Rep. 15: 330 (7 pages). (Year: 2013).*
Minguyan T. et al., "Curcumin induces ABCA1 expression and apolipoprotein A-I-Mediated cholesterol transmembrane in the chronic cerebral hypoperfusion aging rats", The American Journal of Chinese Medicine, vol. 41, No. 5, Jan. 14, 2013, pp. 1027-1042.
Search Report and Written Opinion of PCT/IB2020/056996 of Nov. 20, 2020.

* cited by examiner

Primary Examiner — Russell G Fiebig
(74) Attorney, Agent, or Firm — Silvia Salvadori, P.C.; Silvia Salvadori

(57) ABSTRACT

Association comprising: dry extract of *Bacopa monnieri*, Astaxanthin, Vitamin E, L-theanine and dry extract of *Centella asiatica* for use as an adjuvant in the prevention of vascular dementia, as it is able to reduce the main modifiable risk factors of cognitive vascular impairment (VCI).

11 Claims, 2 Drawing Sheets

FOOD SUPPLEMENT, FOR AS ADJUVANT, FOR PREVENTING VASCULAR DEMENTIA

This application is a U.S. national stage of PCT/IB2020/056996 filed 24 Jul. 2020, which claims priority to and the benefit of Italian Application No. 102019000013707 filed on 1 Aug. 2019, the contents of which are incorporated herein by reference in their entireties.

SUMMARY OF THE INVENTION

The present invention relates to an oral formulation, particularly as an adjuvant for use in the prevention of vascular dementia, in particular in reducing the major modifiable risk factors of vascular cognitive impairment (VCI).

STATE OF THE ART

Vascular dementia (VaD) is one of the most common causes of dementia in elderly people, accounting for 8-10% of all dementia cases and is second only to Alzheimer's disease (AD)[1]. Already in 2002, the Italian Longitudinal Study on Aging (ILSA) estimated a prevalence of dementia in the Italian population between 65 and 84 years of age of 7.2% in women and 5.3% in men. According to the same study, in accordance with European data, in Italy the vascular form represents 22% of dementias, for a total of about 150,000 prevalent cases.

One of the mild forms of VaD is Vascular Cognitive Impairment (VCI). From a clinical point of view, it has been seen that patients with VCI have a deficit in executive functions with relative memory savings[2,3,4] up to more advanced stages, where pseudobulbar affect (dysarthria, dysphagia) and urinary incontinence are often present. Nearly half of people with cognitive vascular impairment (VCI) come to have vascular dementia VaD five years after the first diagnosis of disease. Therefore, the need to identify and manage the risk factors that come into play in cases of VCI as soon as possible is essential to prevent vascular damage and improve patients' quality of life[5]. In addition to advanced age, the risk factors for vascular dementia include: high blood pressure, atherosclerosis, diabetes, heart disease, and stroke. It has also been seen that the massive release of glutamate occurs as a result of brain damage, which is neurotoxic and promotes oxidative stress and therefore inflammation of the neuron[6,7].

Currently there is a lack of effective drug interventions for vascular dementia. Standard treatment focuses largely on symptomatic management and the prevention of further brain damage through the recognition and control of cardiovascular and cerebrovascular risks using, for example, antihypertensives, aspirin, statins, antidiabetics and lifestyle modification. Several classes of anti-AD pharmaceutical agents are used off-label for the symptomatic management of vascular dementia. Cholinesterase (ChE) inhibitors (donepezil, galantamine, and rivastigmine) and NMDA receptor antagonists (memantine) have shown some modest short-term clinical benefits in improving cognitive function; however, most of these studies fail to demonstrate significant improvements in overall functioning, daily living activities, and quality of life. Most of the studies conducted so far have a relatively short duration (5-6 months); therefore, the long-term benefits and safety of these vascular dementia interventions have not been validated[7].

Regarding neuronal damage from oxidative stress, often associated with neurovascular problems such as stroke, it should be noted that the brain is an organ which is highly vulnerable to oxidative stress because metabolic activity is more intense in these tissues and therefore the demand for energy is greater, and more free radicals are produced. This is intrinsic to the oxidative phosphorylation process and represents a potential risk of cell destruction starting with the mitochondria itself. The free radicals produced are readily deactivated by the action of the antioxidant mechanisms (superoxide dismutase, glutathione, catalase). In any case, since no enzyme defensive system is 100% efficient, the overall set of antioxidant enzymes cannot completely neutralize the reactive oxygen produced by the mitochondria. Antioxidant mechanisms can in fact suffer a crisis due to a number of factors and therefore no longer be able to compensate for the production of free radicals by the cells. Oxidative stress occurs in this case: the free radicals react with biological molecules (lipids, proteins, nucleic acids) to cause structural and functional alteration and activate the inflammatory system. Over time, the theory of ageing based on free radicals has evolved into the theory of ageing based on mitochondrial free radicals[8-9]. This theory asserts that overall oxidative damage to mitochondria, aggravated by endogenous metabolic processes and/or exogenous oxidative influences[10], results in a progressive reduction of mitochondrial efficiency. The substantial damage is attributable to the electrons passing through the membranes, which damage the mitochondria and lead to lower energy production. It triggers a vicious circle involving functional damage and diminished energy production. The mitochondria gradually lose their functional integrity and therefore an increasing percentage of oxygen molecules which reach them is converted into ROS. In the case of stroke, the mitochondrial contribution could be decisive: the enormous amount of ROS generated in the neural and glial mitochondria during the ischaemic attack can be devastating for brain tissue[11]. The reduction of neuronal plasticity on a vascular basis is also a consequence of the impairment in vascular endothelial cells' secretion of trophic factors essential for the further regulation of neurogenesis[12]. The metabolic impact of reduced blood flow may be exacerbated by altered transport through the capillary wall. In addition to affecting the structure and function of blood vessels, ageing reduces microvascular plasticity so that capillaries respond less to increases in neuronal activity, although responses to other factors which promote angiogenesis can be preserved. The loss of vascular plasticity certainly affects neuronal plasticity, because neuronal turnover in the adult brain is linked to capillaries and their growth. Trophic factors produced by endothelial cells are important additional regulators of neurogenesis within the adult hippocampus, and the impairment in the secretion of these factors may have repercussions on the elderly brain. Thus, age-related changes in microvascular structure and plasticity contribute to the decline of cognitive function that accompanies brain ageing in multiple ways. To counteract cognitive damage caused by vascular problems, it is rational to apply strategies aimed at reducing the modifiable risk factors underlying the problem as much as possible.

The main modifiable risk factors are:
Neuro-inflammation oxidative stress: the increase in oxygen free radicals leads to neuro-inflammatory activation with negative consequences for neuron function;
Alteration of the supply of oxygen and neuronal trophic: the reduction of blood flow at the neuronal level inevitably leads to trophic suffering and oxygen deficiency which results in a reduction in the plasticity of the neuron;

Alteration of cholinergic neuro-transmission: the decline of mnemonic and cognitive functions are always associated with lower efficiency of acetylcholine-mediated neuro-transmission.

Therefore, in order to reduce cognitive vascular impairment (VCI) globally, one should:
1. Reduce oxidative stress and neuro-inflammation;
2. Induce vasodilation of neural arterioles to promote trophic and oxygenative supply
3. Promote post-synaptic accumulation of acetylcholine to maintain the efficient transmission of electrical signals The object of the present invention is to provide one or more active ingredients capable of:
1. Protecting from neuronal inflammation and from oxidative stress
2. Improving cognitive and mnemonic performance
3. Promoting neuronal plasticity.

L-theanine is a natural substance found in the leaves of *Camellia sinensis*, better known as a tea plant or green tea. The structural similarity of L-theanine with glutamic acid means that it has a high affinity for glutamate receptors. L-theanine is a glutamate antagonist and binds to ionotropic glutamate receptors such as AMPA, kainate and NMDA receptors, which could play an important role in protecting neurons from excess glutamate. In addition to acting on glutamate receptors, animal studies have revealed that L-theanine influences dopamine and serotonin concentrations in the brain, and may have anti-stress effects by inhibiting excitation of the cortical neuron. Recent studies have also shown that L-theanine not only reduces anxiety but also attenuates the increase in blood pressure in adults with a high stress response. The antagonistic mechanisms of glutamate and the reduction of stress hypertension cause L-theanine to protect neurons from oxidative and inflammatory damage, which causes cognitive deficits and dementia[13-15].

*Centella asiatica* is a medicinal herb commonly used in Ayurvedic and Chinese medicine, which thanks to a phytocomplex consisting mainly of terpenes has antioxidant, anti-inflammatory and anti-apoptotic properties. All of these properties could explain why *Centella asiatica* not only strengthens blood vessels but also has a positive influence on brain plasticity. In vivo studies have shown that *Centella asiatica* increases the length of dendrites and also improves the neural dendritic arborization of the CA3 hippocampus in mice affected by neurodegenerative diseases 5. In vitro studies have shown that the effectiveness of *Centella asiatica* extract in improving cognitive functions is linked to its cholinergic properties, in fact it inhibits the action of acetylcholinesterase (AChE), the key enzyme in the pathogenesis of Alzheimer's disease (AD). *Centella* also has antioxidant and anti-inflammatory properties, in vitro studies on neuronal cells have confirmed the protective effect of asiaticoside on the integrity of the neuronal membrane damaged by hyper-production of lactate dehydrogenase caused by ischaemia-hypoxia. The increase in lactate dehydrogenase in the cell supernatant shows a correlation with lipid peroxidation of the cell membrane. The results further confirmed that asiaticoside can also directly inhibit lipid peroxidation of the membrane, thereby reducing neuronal necrosis and protecting nerve cells[16-18].

The components responsible for the pharmacological effects of *Bacopa monnieri* include alkaloids, saponins, sterols. Some components (the alkaloids brahmin and herpestin, saponins, D-mannitol, acid A, monnierin) were isolated in India more than 40 years ago. Other active constituents have been subsequently identified and include betullic acid, stigmasterol, beta-sitosterol and some bacosides and bacosaponins. The components responsible for cognitive effects are thought to be bacosides A and B, where the latter differs only in optical activity and is probably an artefact produced during the bacoside A isolation process. Triterpenoid saponins and their bacosides are responsible for *Bacopa*'s ability to increase nerve impulse transmission. Bacosides help repair damaged neurons by increasing protein kinase activity, facilitating neuronal synthesis, contributing to the restoration of synaptic activity, and improving nerve impulse transmission. Based on the results of animal model studies, bacosides can be said to exert antioxidant activity in the hippocampus, frontal cortex, and striatum. *Bacopa monnieri* extract in the animal model and in isolated arteries in vitro: reduces blood pressure by releasing nitric oxide from the endothelium, with additional effect on vascular smooth muscle $Ca^{2+}$ homoeostasis; injected intravenously, it reduces systolic and diastolic pressure without interfering with heart rate, induces vasodilation in isolated arteries. *Bacopa monnieri* is defined as a nootropic component as it promotes the release of cholinergic neurotransmitters and their post-synaptic concentration by reducing acetylcholinesterase[19-27].

Among many properties, astaxanthin has an anti-inflammatory and antioxidant action and protects the plasma membrane and the mitochondrial double membrane, improving its functions and thus increasing the ability of the mitochondria to produce energy[28-30].

The biological action of vitamin E is due to its antioxidant capacity: it prevents the spread of polyunsaturated fatty acid (PUFA) oxidation by sequestering peroxylipid radicals. This is the fundamental function of vitamin E in animal tissues and particularly in cell membranes, where tocopherol is associated with PUFA in phospholipids.

CN 107 789 429 A (SHANDONG YZANDER MEDICAL TECHNOLOGY CO) (XP002798468), describes an extract of *Bacopa monnieri* containing saponin for use in the treatment of vascular dementia.

KR 2012 0051458 A (XP002798476) describes a method for preparing a composition for preventing vascular dementia by combining phosphatidylserine and astaxanthin with phospholipids derived from Krill.

CN 105 287 985 A (XP002798477), describes a composition for use in treating senile dementia, in which the composition comprises, among other active ingredients, vitamin E.

JP 2000 229854 A (XP002798469) describes theanine as an active substance for use in the treatment and prevention of vascular dementia.

CN 102 389 437 (XP002798470) describes a composition containing *Centella asiatica* triterpenoids for preventing and treating vascular dementia.

WO 03/003981 A2 describes the enhancement of mental functions by a composition comprising *Bacopa monniera*, docosohexaenoic acid and Vitamin E, among others.

CN 109 419 800 A (XP002798471) describes a composition for use in the treatment of vascular dementia comprising DHA and vitamin E among the other active ingredients.

WO 2013/066151 A1 describes a composition for use in the treatment of Alzheimer's dementia comprising docosahexaenoic acid and Vitamin E among others.

Mingyuan T. et al "Curcumin Induces ABCA1 Expression and Apolipoprotein A-I-Mediated Cholesterol Transmembrane in the Chronic Cerebral Hypoperfusion Aging rats" The American Journal of Chinese Medicine" World Scientific US, Vol. 41 pages 1027-1042-XP009519445, describes the use of curcumin as a new, different approach to cerebrovascular diseases thanks to its ability to modulate transmembrane cholesterol transport in the brain.

SUMMARY OF THE INVENTION

The applicant has now found an association of active ingredients which can reduce the main modifiable risk factors of vascular cognitive impairment (VCI) and can therefore be used as an adjuvant in the treatment of vascular dementia.

The object of the present invention is therefore the aforementioned association consisting of: dry extract of *Bacopa monnieri*, Astaxanthin, Vitamin E, L-theanine and dry extract of *Centella asiatica* and optionally at least one of the following active ingredients selected from Palmitoylethalonamide (PEA), eleutherococcus, *Theobroma cacao*, for use as an adjuvant in the prevention of vascular dementia, in which said association is administered in the form of an oral formulation, preferably a tablet, which contains it as the only active ingredient, in combination with suitable excipients and/or diluents and in said oral formulation:

*Bacopa monnieri* is present in an amount between 70 to 200 mg, more preferably 100 mg with a minimum titre in bacosides of 10%, preferably of 20%;

astaxanthin is present in said combination with a minimum content of 1 mg, preferably 2 mg;

vitamin E, preferably as vitamin acetate, is present in said association in a maximum amount of 60 mg, preferably 30 mg;

L-theanine is present in said combination in amounts ranging from 150 to 300 mg, more preferably 200 mg.

*Centella asiatica* is present in amounts of 75 to 250 mg, more preferably 150 mg with a minimum titre in tot terpen (as asiaticoside) of 10%.

DETAILED DESCRIPTION OF THE INVENTION

Figure 1:
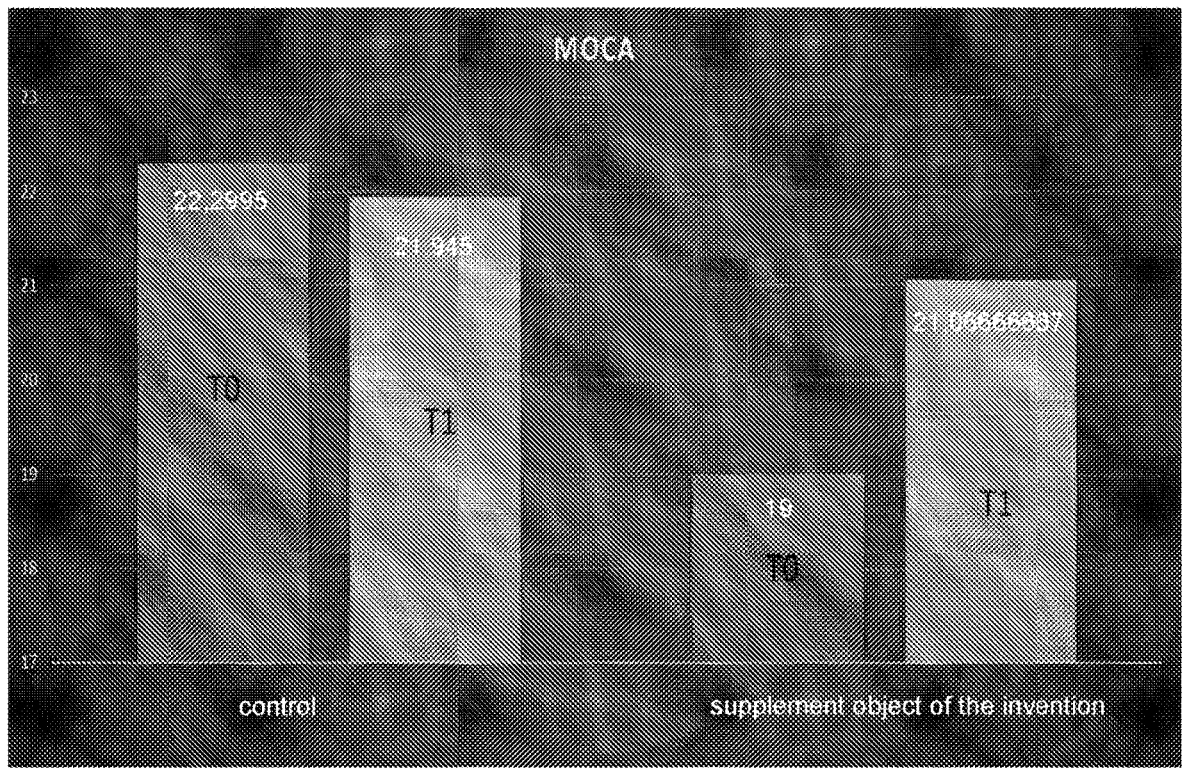
FIG. 1 shows the results at time T0, i.e., at the beginning of the study and at time T1 after 3 months, of the MoCa test (Montreal Cognitive Assessment Test) conducted on a total of 35 patients with mild VCI of which: 20 represent the control group, while the remaining 15 represent the treated group to which the supplement has been administered once a day as a tablet, whose composition is given in example 1.

For the purposes of the present invention the definition "comprising" does not exclude the possibility that after such definition there are additional components in addition to those expressly listed after such definition; on the contrary the definition "consisting of" excludes the possibility that there are additional components in addition to those expressly listed after such definition.

According to a preferred solution of the association for use object of the present invention, the association consists of the aforementioned 4 active substances *Bacopa monnieri*, Astaxanthin, Vitamin E, L-theanine and dry extract of *Centella asiatica*.

According to another particularly preferred solution, in addition to the aforementioned active ingredients, the association for use according to the present invention consists not only of the aforementioned four active ingredients but also optionally at least one of the following active ingredients selected from Palmitoylethanolamide (PEA), Eleuterococcus, *Theobroma cacao*.

The association is administered for use according to the present invention in the form of an oral formulation, which contains it as the only active ingredient in combination with suitable excipients and/or diluents.

More preferably said oral formulation is a food supplement.

Still more preferably said oral formulation or food supplement is in tablet form.

The oral formulation, preferably in tablet form, for use according to the present invention contains as the only active ingredient the aforesaid association in which:

the dry extract of *Bacopa monnieri* is contained in an amount between 70 to 200 mg, more preferably 100 mg with a minimum titre in bacosides of 10%, preferably 20%;

astaxanthin is contained in said association with a minimum content of 1 mg, preferably 5 mg;

vitamin E, preferably as vitamin E acetate, is contained in said association in a maximum amount of 60 mg, preferably 30 mg;

L-theanine is contained in said association in amounts ranging from 150 to 300 mg, more preferably 200 mg Dry extract of *Centella asiatica* in amounts of 75 to 250 mg, more preferably 150 mg with a minimum titre in tot terpen (as asiaticoside) of 10%.

The astaxanthin is preferably contained in a dry extract of *Haematococcus pluvialis* Flotow algae with a minimum astaxanthin titre of 2%, more preferably 5%.

Preferably the tablet containing as the only active ingredient the association for use according to the present invention is administered 1 or 2 times daily.

The composition of the food supplement in the form of a tablet containing as the only active ingredient the association for use according to the present invention is shown below in example 1 for illustrative purposes, and example 2 shows a clinical study demonstrating the efficacy of the tablet, whose composition is reported in example 1, against VCI and thus in the prevention of vascular dementia.

Example 1—Food Supplement Formula in the Form of a Coated Tablet

| ACTIVE INGREDIENTS | For a 1.1 g tablet |
|---|---|
| L-Theanine 98% | 200 mg |
| Centella (*Centella asiatica* (l.) urb., leaves) dry extract | 150 mg |
| Vitamin E acetate | 30 mg |
| Bacopa (*Bacopa monnieri* (1.) pennel, leaves) dry extract 20% | 100 mg |
| *Haematococcus pluvialis* Flotow - Astaxanthin powder 5% | 2 mg astaxanthin |

-continued

| EXCIPIENTS | For a 1.1 g tablet |
|---|---|
| Cellulose - E 460 (i) | 250 mg |
| Calcium phosphates - E 341 (ii) | 220 mg |
| Cross-linked sodium carboxymethylcellulose - E 468 | 30 mg |
| Silicon dioxide - E 551 | 20 mg |
| Fatty acid magnesium salts - E 470b | 20 mg |
| Sepifilm White LP 770 White | 17.6 mg |
| Glycerol - E 422 | 3.5 mg |
| Iron oxides and hydroxides - E172 | 1.9 mg |

Example 2—Clinical Study

The purpose of the present study is to verify whether the supplement object of the present invention, administered in the form of swallowable tablets once a day, can promote cognitive functions and memory in subjects with vascular cognitive impairment (VCI), preventing the aggravation of neuronal damage.

No. Patients Tested and Inclusion/Exclusion Criteria.

Data from 35 patients with VCI, which can be hypothesized on the basis of co-morbidity with vascular disorders (small vessel disease, arterial hypertension, atherosclerosis, micro stroke or mild stroke, etc.) and/or metabolic diseases, are analysed, together with a raw MoCA test score between 15 and 24 (+1 point on schooling <13 years) and interview with the caregiver attesting to changes in cognitive function and memory. The patients are of both sexes and over the age of 60.

Of the 35 patients, 15 belong to the group which took the supplement object of the invention, 20 patients belong to a control group which did not take the supplement.

All the patients with previous hospitalizations for stroke and haemorrhagic stroke, patients with other primary neurological disorders such as multiple sclerosis, Parkinson's disease, encephalitis and Alzheimer's disease sufficient to explain cognitive impairment, patients with sufficiently severe conditions such as brain tumours and major depression, patients with an active diagnosis of drug or alcohol abuse/dependence, patients with kidney disease, patients already treated with medications to manage cognitive impairment and dementias, patients treated with benzodiazepines and neuroleptic drugs, patients with known or suspected intolerance to at least one of the components of the product were excluded from the trial.

Dosage: 1 tablet/day (on a full stomach).
Data over 3 consecutive months of observation
T0→baseline
T1→after three months of observation The efficacy of the supplement object of the present invention was evaluated through the analysis of the MOCA questionnaire of the treated group versus the untreated control group:

Montreal Cognitive Assessment scale (MoCA): It is a fairly quick tool, used as screening for mild cognitive impairment, often on a vascular basis. It allows to verify different functional areas: attention, concentration, executive functions, memory, language, visual-constructive skills, abstraction, calculation, orientation. Score range: 0-30 points (zero worst case, 30 no cognitive impairment (CI))

GDS test (Geriatric depression scale): questionnaires which measure depressed mood in geriatric subjects. It has a score ranging from a minimum of "zero" (absent disorder) to a maximum of "thirty" (worst disorder). The severity of depression is therefore represented as follows: 0 to 10 absent, 11 to 16 mild/moderate depression, 17 or higher severe depression.

Trail Making A (TMT-A) test evaluates the capacity for spatial planning in a visual-motor type task. The subject must sequentially join the numbers 1 through 25 with a pencil. The task must be completed as quickly as possible. Errors must be corrected immediately by the examiner.

Results

Figure 2:
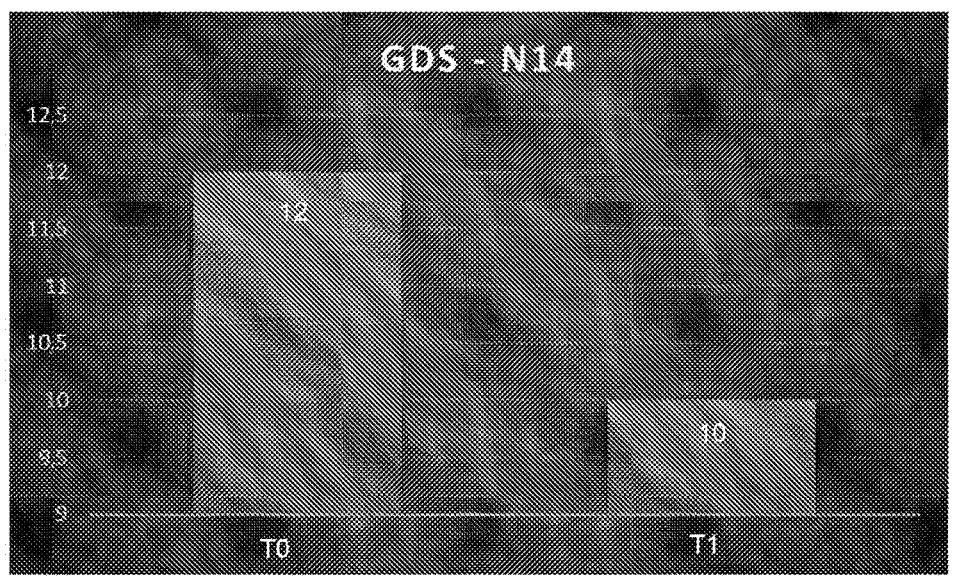
FIG. 2 shows the results of the Geriatric Depression Scale (GDS) test at time T0 at the beginning of the study and time T1 after 3 months in 14 patients who received the supplement as a tablet once daily, whose composition is shown in the example.
Figure 3:
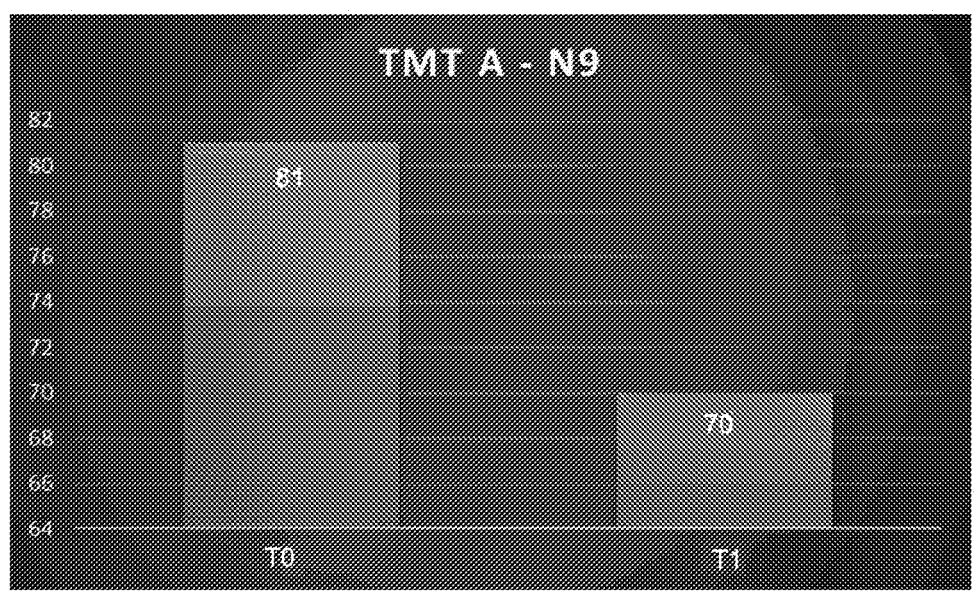
FIG. 3 shows the results at time T0 at the beginning of the study and time T1 after 3 months of the Trail Making A (TMTA) test conducted on 9 patients who received the supplement as a tablet once daily, whose composition is shown in the example.

The results obtained for the three tests are shown in FIGS. 1,2 and 3, respectively.

FIG. 1 (MoCA test) shows the score rise from 19 to 21 in the first trimester in the group treated with the supplement object of the invention. These data suggest an impacting action of the supplement of the present invention in the quarter; on the contrary, there is a slight deterioration in the control group.

FIG. 2: The GDS test conducted on 14 patients shows that the mood disorder has changed from mild/moderate (12) to absent (10).

FIG. 3: The TMT-A test conducted on 9 patients shows that the mean execution time of 81 sec at T0 is reduced to approximately 70 sec. Again, the supplement object of the present invention acts positively in the quarter.

CONCLUSIONS

Specifically, it improves the response to tests on the status of global memory investigated through MoCA tests (attention concentration, executive functions, memory, language, visual-constructive skills, abstraction, calculation, orientation), it also improves the capacity of spatial planning in a visual-motor type task (TMT-A). Subjects have a higher perception of psychic/humoral well-being (GDS).

BIBLIOGRAFIA

1. Wolf-Dieter Heiss et al. Neuroimaging in vascular cognitive impairment: a state-of-the-art review. BMC Medicine. 2016
2. Anna Maria Mello et al. Demenza vascolare sottocorticale: inquadramento clinico e diagnostico-terapeutico. www.sisa.it. 2011
3. Yang Yu et al. How does white matter microstructure differ between the vascular and amnestic mild cognitive impairment? Oncotarget. 2017
4. JOUKJE M. OOSTERMAN and ERIK J. A. SCHERDER. Distinguishing between Vascular Dementia and Alzheimer's Disease by Means of the WAIS: A Meta-analysis. Journal of Clinical and Experimental Neuropsychology. 2006
5. Suvarna Alladi et al. Vascular cognitive impairment: Current concepts and Indian perspective. Annals of Indian Academy of Neurology. 2010
6. Vladimir Hachinski et al. National Institute of Neurological Disorders and Stroke—Canadian Stroke Network Vascular Cognitive Impairment Harmonization Standards. Stroke. 2007.
7. Dennis Chang et al. Herbal Medicine for the Treatment of Vascular Dementia: An Overview of Scientific Evidence Hindawi Publishing Corporation Evidence-Based Complementary and Alternative Medicine. 2016.

8. Valentine J S, Wertz D L, Lyons T J, et al. The dark side of dioxygen biochemistry. Curr Opin Chem Biol 1998; 2:253-262.
9. Schipper H M. Brain iron deposition and the free radical-mitochondrial theory of ageing. Ageing Res Rev 2004; 3:265-301
10. Kidd P M, Levine S A. Liver biotransformation of xenobiotic chemicals, foods, and drugs to free radical oxidants. In: Levine S A, Kidd P M, eds. Antioxidant Adaptation. Its Role in Free Radical Pathology. San Leandro, CA: Biocurrents/Allergy Research Group; 1985.
11. Harman D. The biologic clock: the mitochondria? J Am Geriatric Soc 1972; 20:145-147.
12. William E. Sonntag, Delrae M. Eckman, Jeremy Ingraham, D R. Riddle. Regulation of Cerebrovascular Aging. In: Brain Aging: Models, Methods, and Mechanisms. Riddle D R, editor. Boca Raton (FL): CRC Press; 2007.
13. Takami KAKUDA. Neuroprotective Effects of the Green Tea Components Theanine and Catechins. Biol. Pharm. Bull 2002
14. Kenta Kimura et al. L-Theanine reduces psychological and physiological stress responses. Biological Psychology. 2007
15. Hidehiko Yokogoshi et al. Reduction Effect of Theanine on Blood Pressure and Brain Hydroxyindoles in Spontaneously Hypertensive Rats. Bioscience, Biotechnology, and Biochemistry. 1995
16. KunMarisa Farhana et al. Effectiveness of Gotu Kola Extract 750 mg and 1000 mg Compared with Folic Acid 3 mg in Improving Vascular Cognitive Impairment after Stroke. Hindawi Publishing Corporation Evidence-Based Complementary and Alternative Medicine. 2016
17. Tao Sun et al. Nerve Protective Effect of Asiaticoside against Ischemia-Hypoxia in Cultured Rat Cortex Neurons. Med Sci Monit. 2015
18. Ilkay Erdogan Orhan. *Centella asiatica* (L.) Urban: From Traditional Medicine to Modern Medicine with Neuroprotective Potential. Hindawi Publishing Corporation Evidence-Based Complementary and Alternative Medicine. 2012
19. Srithi Srinath/J. Pharm. Sci. & Res. Vol. 6(10), 2014, 331-333
20. Alternative Medicine Review ♦ Volume 9, Number 1 ♦ 2004
21. Hou C C, Lin S J, Cheng J T, Hsu F L. Bacopaside III, bacopasaponin G, and bacopasides A, B, and C from *Bacopa monniera*. J Nat Prod 2002; 65:1759-1763.
22. Mahato S B, Garai S, Chakravarty A K. Bacopasaponins E and F: two jujubogenin bisdesmosides from *Bacopa monniera*. Phytochemistry 2000; 53:711-714.
23. Chakravarty A K, Sarkar T, Masuda K, et al. Bacopaside I and II: two pseudojujubogenin glycosides from *Bacopa monniera*. Phytochemistry 2001; 58:553-556.
24. Singh H K, Dhawan B N. Neuropsychopharmacological effects of the Ayurvedic nootropic *Bacopa monniera* Linn. (Brahmi). Indian J Pharmacol 1997; 29:S359-S365.
25. Bhattacharya S K, Bhattacharya A, Kumar A, Ghosal S. Antioxidant activity of *Bacopa monniera* in rat frontal cortex, striatum, and hippocampus. Phytother Res 2000; 14:174-179.
26. Kamkaew N et al. *Bacopa monnieri* and its constituents is hypotensive in anaesthetized rats and vasodilator in various artery types. J Ethnopharmacol. 2011
27. Tatimah Peth-Nui et al. Effects of 12-Week *Bacopa monnieri* Consumption on Attention, Cognitive Processing, Working Memory, and Functions of Both Cholinergic and Monoaminergic Systems in Healthy Elderly Volunteers. Evidence-Based Complementary and Alternative Medicine. 2012
28. McNulty H P, Byun J, Lockwood S F, et al. Differential effects of carotenoids on lipid peroxidation due to membrane interactions. Xray diffraction analysis. Biochim Biophys Acta 2007; 1768:167-174.
29. Ranga Rao Ambati Astaxanthin: Sources, Extraction, Stability, Biological Activities and Its Commercial Applications—A Review Mar. Drugs 2014
30. Wolf A M, Asoh S, Hiranuma H, et al. Astaxanthin protects mitochondrial redox state and functional integrity against oxidative stress. J Nutr Biochem 2010; 21:381-389.
31. Kontush K, Schekatolina S. Vitamin E in neurodegenerative disorders: Alzheimer's disease. Ann N Y Acad Sci 2004; 1031:249-262.

The invention claimed is:

1. A method for reducing the main modifiable risk factors of vascular cognitive impairment (VCI) comprising orally administering an oral formulation comprising an association consisting of *Bacopa monnieri*, astaxanthin, vitamin E, L-theanine and *Centella asiatica* as the active ingredient and optionally at least one of the following active ingredients selected from the group consisting of palmitoylethalonamide (PEA), eleutherococcus and *Theobroma cacao* wherein
   i) said association is in the form of an oral formulation, said oral formulation containing said association as the only active ingredient in combination with suitable excipients and/or diluents, and in said oral formulation:
   *Bacopa monnieri* is contained in an amount between 70 to 200 mg with a minimum titre in bacosides of 10%;
   astaxanthin is contained in said association in a minimum content of 1 mg;
   vitamin E is contained in said association in a maximum amount of 60 mg;
   L-theanine is contained in the said association in amounts ranging from 150 to 300 mg;
   *Centella asiatica* is present in amounts of 75 to 250 mg with a minimum titre in tot terpen (as asiaticoside) of 10%,
   ii) said main risk factor are neuro-inflammation due to oxidative stress, alteration of oxygen supply and neuronal trophic alteration or alteration of neurotransmission mediated by acetylcholine.

2. The method according to claim 1, wherein said oral formulation is a food supplement.

3. The method according to claim 1, wherein said oral formulation, is administered once or twice a day.

4. The method according to claim 1, wherein said oral formulation is a tablet.

5. The method according to claim 1, wherein said *Bacopa monnieri* is contained in an amount of 100 mg.

6. The method according to claim 1, wherein in said *Bacopa monnieri* the minimum titre in bacoside is 20%.

7. The method according to claim 1, wherein said astaxanthin is contained in said association with a minimum content of 2 mg.

8. The method according to claim 1, wherein said vitamin E is vitamin acetate.

9. The method according to claim 1, wherein said vitamin E is contained in said association in a maximum amount of 30 mg.

10. The method according to claim 1, wherein said theanine is contained in said combination in amounts of 200 mg.

11. The method according to claim 1, wherein said *Centella asiatica* is present in amount of 150 mg.

* * * * *